United States Patent [19]

John et al.

[11] 4,302,440
[45] Nov. 24, 1981

[54] EASILY-SWALLOWED, POWDER-FREE AND GASTRIC-DISINTEGRABLE ASPIRIN TABLET THINLY-COATED WITH HYDROXYPROPYL METHYLCELLULOSE AND AQUEOUS SPRAY-COATING PREPARATION THEREOF

[75] Inventors: Phillip M. John, East Greenbush; Raymond J. Belanger, Rensselaer; Myron Paikoff, Colonie, all of N.Y.

[73] Assignee: Sterling Drug Inc., New York, N.Y.

[21] Appl. No.: 174,249

[22] Filed: Jul. 31, 1980

[51] Int. Cl.³ .............................................. A61K 9/36
[52] U.S. Cl. ........................................... 424/35; 427/3
[58] Field of Search ............................... 424/35; 427/3

[56] References Cited

U.S. PATENT DOCUMENTS

| | | | |
|---|---|---|---|
| 3,256,111 | 6/1966 | Singiser | 424/35 |
| 3,383,236 | 5/1968 | Brindamour | 424/35 |
| 3,388,041 | 6/1968 | Gans et al. | 424/35 |
| 3,907,983 | 9/1975 | Seth | 424/35 |
| 3,981,984 | 9/1976 | Signorino | 424/35 X |
| 4,001,390 | 1/1977 | Ohno et al. | 424/35 |
| 4,154,636 | 5/1979 | Motoyama et al. | 424/35 X |
| 4,167,558 | 9/1979 | Sheth et al. | 424/35 |
| 4,226,849 | 10/1980 | Schor | 424/35 |

Primary Examiner—Shep K. Rose
Attorney, Agent, or Firm—Robert K. Bair; B. Woodrow Wyatt

[57] ABSTRACT

A method for preparing an easily-swallowed, powder-free, gastric-disintegrable and thinly-coated aspirin tablet, which does not have the characteristic aspirin taste, does not produce the esophageal discomfort of an uncoated aspirin tablet and does not disintegrate in the stomach materially slower than the uncoated aspirin tablet, which comprises aqueous spray-coating hydroxypropyl methylcellulose onto all exterior surfaces of an aspirin tablet, the amount of hydroxypropyl methylcellulose being between 0.5 and 2.0 parts by weight per 100 parts by weight of the aspirin tablet. An aqueous solution of 2% to 15% by weight of hydroxypropyl methylcellulose and about 15% to 25% w/w of a plasticizer based on hydroxypropyl methylcellulose is sprayed onto uncoated aspirin tablets in a slowly rotating baffled pan in a chamber equipped to measure and control both inlet and outlet air flow rates and both inlet and outlet air temperatures, said air flow rates and temperatures being sufficient to insure rapid evaporation of the water and to provide an evenly-applied thin coating of hydroxypropyl methylcellulose onto the uncoated tablets without causing their decomposition and/or physical disintegration. Preferred pan-rotation speeds, inlet and outlet air flow rates and temperatures are given. Other aspects of the invention are said thinly-coated tablets and said coated tablets when produced by said aqueous spray-coating method.

24 Claims, No Drawings

EASILY-SWALLOWED, POWDER-FREE AND GASTRIC-DISINTEGRABLE ASPIRIN TABLET THINLY-COATED WITH HYDROXYPROPYL METHYLCELLULOSE AND AQUEOUS SPRAY-COATING PREPARATION THEREOF

BACKGROUND OF THE INVENTION (a) Field of the Invention

This invention relates to a coated aspirin tablet and its preparation. In particular, the invention relates to an aqueous spray-coating method of preparing an easily-swallowed, powder-free and gastric-disintegrable aspirin tablet thinly-coated with hydroxypropyl methylcellulose and the tablet produced thereby.

(b) Description of the Prior Art

Aspirin tablets historically have been difficult to film coat as they are friable, dusty, and easily dissolved by water and organic solvents. Aspirin itself is readily decomposed by moisture and heat. Successful films have been applied from organic solvents using air as well as airless spray processing primarily because of the low flash points and rapid evaporation of the solvents involved.

S. F. Jeffries U.S. Pat. No. 3,149,040, issued Sept. 15, 1964, shows thin film coating of tablets with a particular mixture of cellulose acetate phthalate, a polyoxyethylene derivative of polypropylene glycol and plasticizer, said mixture applied in a non-aqueous system. No such coated aspirin tablets are shown. Moreover, nonaqueous coating systems are now undesirable from an environmental standpoint.

J. L. Anderson et al. U.S. Pat. No. 3,341,416, issued Sept. 12, 1967, discloses the encapsulation of minute particles of aspirin in ethylcellulose, using a cyclohexane solution of the latter. The encapsulated particles are said to provide "a minimum amount of release" of aspirin "in the stomach" and a continuing release of aspirin "slowly all along the extent of the intestinal tract."

E. H. Gans et al. U.S. Pat. No. 3,388,041, issued June 11, 1968, teaches the preparation of a high dosage sustained release tablet containing aspirin which comprises granulating aspirin with a solution of a mixture of hydroxypropyl methylcellulose and ethylcellulose in a volatile organic solvent, drying the coated granules and compressing the granules into sustained released tablets, which slowly release aspirin "for a period of up to twelve hours". Gans et al. also discloses a preferred two-ply laminate tablet using two different aspirin granulation compositions, namely: (1) said granulated aspirin coated with the combination of hydroxypropyl methylcellulose and ethylcellulose to provide slow release of aspirin over a period of up to twelve hours; and, (2) a composition of an uncoated mixture of aspirin and starch to provide rapid release of aspirin.

H. R. Hawthorn Australian Pat. No. 477,515, published July 17, 1975, shows the application to aspirin tablets of an enteric coating comprising a mixture of hydroxypropyl methylcellulose phthalate and ethyl cellulose using a solution of the coating materials in a mixture of methylene dichloride and alcohol, thereby providing a tablet with a coating of sufficient thickness to pass unchanged through the stomach.

R. E. Singiser U.S. Pat. No. 3,256,111, issued June 14, 1966, shows a method of applying a protective glossy coating to previously coated and dried tablets by spray-coating hydroxypropyl methylcellulose in a non-aqueous solvent. Although Singiser appreciated the advantages of hydroxypropyl methylcellulose being soluble in water as well as in organic solvents, he used only its non-aqueous solutions in his spray-coating method. The only previously coated tablets gloss-coated by Singiser are vitamin tablets.

Y. Tuji U.S. Pat. No. 3,477,864, issued Nov. 11, 1969, shows a process for coating tablets, etc., with a moisture-preventing and thermostable film, said process which comprises: (a) preparing a coating composition by dissolving hydroxypropyl methylcellulose in a mixture of at least one low boiling aliphatic halide and at least one other selected low boiling organic solvent and adding to the solution one of three prescribed sealing agents; (b) spraying the composition onto the tablets, etc., being rolled in a usual coating pan; (c) drying the coated tablets, etc.; and (d) repeating the spraying and drying. The only tablets shown contain sodium chloride, sucrose, corn starch and magnesium stearate. The solvent system used to prepare the coating composition is environmentally undesirable and the disintegration times of the coated tablets actually are greater than that of the uncoated tablets.

An article entitled "Coating tablets with water based solutions" [Manufacturing Chemist & Aerosol News, p. 31, January 1976], which is based on trials by Manesty Machines Ltd. Liverpool, England, recommends very low viscosity grades (between 6 and 15 cps) of hydroxypropyl methylcellulose, preferably with a water-soluble plasticizer, and slowly rotating pan speeds, e.g., as low as $2\frac{1}{2}$ rpm. Problems of aqueous spray-coating of tablets are discussed. There is no mention of any particular pharmaceutical ingredients in the uncoated tablets. This publication states that "the plasticisers that can be used is limited to water solubles"; however, it states that "glycerol and propylene glycol were not particularly successful". Although this publication generally states "that even water-sensitive tablets can be successfully coated without the penetration of water affecting the material", it is believed that such a general statement would not lead one skilled in the art of pharmaceutical production to applicants' process described below. It is well known that manufacturers of aspirin and aspirin tablets, from start to finish, scrupulously avoid all exposure of this analgesic or its tablets to water. In fact, manufacturers of aspirin tablets control the humidity of processing rooms to prevent decomposition of the aspirin and its tablets. Accordingly, it is believed to be non-obvious to purposely spray an aqueous coating solution with concurrent heating onto uncoated aspirin tablets as unexpectedly done successfully by applicants in their process described hereinbelow.

S. Ohno et al. U.S. Pat. No. 4,017,647, issued Apr. 12, 1977, relates to a "Method for Providing Enteric Coatings on Solid Dosage Forms". Example 3 of this patent shows aqueous spray-coating of aspirin tablets with hydroxypropyl methylcellulose phthalate, treating the coated tablets with 3 N hydrochloric acid at 20° C., washing the acid-treated product with water and drying the washed enteric-coated tablets. These tablets, unlike applicants' tablets discussed below, "remained unchanged in the simulated gastric fluid and were completely disintegrated in the simulated intestinal fluid within a period of from 4 minutes and 50 seconds to 5 minutes and 30 seconds". In contrast, applicants' coated tablets disintegrate in simulated gastric fluid in less than one minute.

P. R. Sheth U.S. Pat. No. 4,167,558, issued Sept. 11, 1979, relates to a sustained release aspirin tablet containing from about 20% by weight to about 75% by weight of one or a mixture of hydrocolloids, e.g., hydroxypropyl methylcellulose, said tablet which provides, upon contact with gastric fluid, a water impermeable barrier on its surface and which acquires and maintains a bulk density of less than one thereby being buoyant in said fluid and remaining buoyant in the gastric fluid of the stomach until substantially all of the aspirin contained therein is released over a prolonged period.

SUMMARY OF THE INVENTION

In a method aspect, the invention relates to the method for preparing an easily-swallowed thinly-coated aspirin tablet which comprises aqueous spray-coating hydroxypropyl methylcellulose onto all exterior surfaces of an aspirin tablet.

In a composition aspect, the invention relates to an easily-swallowed aspirin tablet thinly coated with hydroxypropyl methylcellulose, said coating being sufficiently thin as to not materially alter the gastric rate of disintegration as compared with the uncoated aspirin tablet.

In a composition-by-method aspect, the invention relates to the easily-swallowed thinly-coated aspirin tablet when produced by the method which comprises aqueous spray-coating hydroxypropyl methylcellulose onto all exterior surfaces of an aspirin tablet.

DETAILED DESCRIPTION INCLUSIVE OF PREFERRED EMBODIMENTS

In a method aspect, the invention resides in the method for preparing an easily-swallowed, powder-free, gastric-disintegrable and thinly-coated aspirin tablet which does not have the characteristic aspirin taste and does not produce the esophageal discomfort of an uncoated aspirin tablet and which does not disintegrate in the stomach materially slower than the uncoated aspirin tablet, which comprises aqueous spray-coating hydroxypropyl methylcellulose onto all exterior surfaces of an aspirin tablet, the amount of hydroxypropyl methylcellulose being between 0.5 and 2.0 parts by weight per 100 parts by weight of the aspirin tablet. In an embodiment of this method aspect, an aqueous solution of 2% and to 15% by weight of hydroxypropyl methylcellulose and about 15% to 25% w/w of a plasticizer based on the weight of hydroxypropyl methylcellulose is sprayed onto uncoated aspirin tablets in a slowly rotating baffled pan in a chamber equipped to measure and control both inlet and outlet air flow rates and both inlet and outlet air temperatures, the inlet and outlet air rates and temperatures being sufficient to insure rapid evaporation of the water and to provide an evenly-applied thin coating of hydroxypropyl methylcellulose onto the uncoated tablets without causing their decomposition and/or physical disintegration. In a preferred embodiment of this method aspect, the pan is rotated at about 2.5 to 8.0 rpm, the inlet air flow rate is maintained at about 1500 to 4000 cubic feet per minute at a temperature ranging from about 35° C. to 90° C. and the outlet air flow rate is maintained at about 2000 to 5000 cubic feet per minute at a temperature ranging from about 35° C. to 80° C. The dew point of the inlet air is monitored and regulated at about 2° C. to 15° C., the air being filtered to remove dust and any other contaminants. In a particularly preferred method embodiment, a 48" perforated coating pan is used, the inlet air flow rate is maintained within the range of about 1700 to 2500 cubic feet per minute at a temperature range of about 60° C. to 80° C., the outlet air flow rate is maintained within the range of about 2100 to 2700 cubic feet per minute at a temperature range of about 50° C. to 70° C., and there is used a 4% to 8% by weight solution of hydroxypropyl methylcellulose in water containing about 15% to 25% w/w of glyceryl triacetate as plasticizer based on the weight of hydroxypropyl methylcellulose.

In a composition aspect, the invention resides in an easily-swallowed, powder-free and gastric-disintegrable aspirin tablet thinly-coated on all of its exterior surfaces with hydroxypropyl methylcellulose, said coating being sufficiently thin as to not materially alter the gastric rate of disintegration as compared with the uncoated aspirin tablet, and which coated tablet does not have the characteristic aspirin taste and does not produce the esophageal discomfort of the uncoated aspirin tablet. A preferred embodiment of this aspect of the invention is the aspirin tablet uniformly coated with about 0.5 to 2 parts by weight of hydroxypropyl methylcellulose per 100 parts by weight of aspirin tablet and about 15 to 25% w/w of a plasticizer based on the weight of hydroxypropyl methylcellulose, where hydroxypropyl methylcellulose produces a viscosity between 13.0 and 18.0 centipoises when measured as a 2% by weight aqueous solution. A particularly preferred embodiment is said preferred embodiment where the hydroxypropyl methylcellulose contains not less than 28.0% and not more than 30.0% of methoxy and not less than 7.0% nor more than 12.0% of hydroxypropoxy and the plasticizer is glyceryl triacetate.

In a composition-by-method aspect, the invention resides in said composition aspect when produced by said method aspect. Preferred and particularly preferred embodiments of this aspect of the invention are said preferred and particularly preferred embodiments of said composition aspect of the invention when produced by said preferred and particularly preferred embodiments of said method aspect of the invention.

The method aspect of the invention was developed to apply a thin coating or film of hydroxypropyl methylcellulose from an aqueous system to the surface of conventional aspirin tablets for the purposes of: (a) greatly improving the ease with which such tablets may be swallowed; (b) greatly reducing is not eliminating the incidence of epigastric distress; (c) providing a tablet readily disintegrable in the stomach; (d) eliminating the dust of packaging and handling of finished aspirin tablets; and, (e) improving their appearance and salability. Specific benefits provided by the method and composition aspects of the invention include: (a) method covers dusty tablet surface with a slick shiny film, reducing powdery perception; (b) method completely masks characteristic taste of aspirin, thereby eliminating nausea and/or discomfort due to the taste of uncoated aspirin tablets; (c) tablet can be easily swallowed, especially by children and elderly people who often have difficulty in swallowing tablets; (d) tablet easily and quickly passes through mouth, throat and esophagus to the stomach without disintegration, thereby eliminating epi-gastric distress, e.g., "heart burn" and throat irritation caused by ingesting uncoated aspirin tablets; (e) disintegrates quickly in the stomach, thereby providing aspirin for rapid entry into the blood stream.

The method aspect of the invention provides the following advantages: (a) can be applied to aspirin tablets of commercial production without special treatments or reformulation to increase hardness or durability to withstand breakage during film-coating manipulations; (b) produces aspirin tablets which resist disintegration in the mouth but still disintegrate in the stomach or simulated gastric fluid in less than one minute; (c) does not change stability or shelf life of original tablets; (d) does not slow the disintegration of the tablet in the stomach or in simulated gastric fluid test systems, i.e., USP Disintegration Test; (e) is an environmentally safe process, i.e., it does not involve the use of organic solvents in the film-coating solutions, such as alcohol, methylene chloride, chlorothene, acetone, ether, and the like; (f) does not alter the dissolution profile; (g) does not result in measurable differences in salicylate blood levels compared with uncoated tablet; (h) improves the appearance of the product and prevents the formation of tablet dust inside bottles of packaged goods; (i) reduces difficulties encountered with high-speed automatic packaging equipment by eliminating crumbling tablets and loose powder; and, (j) the transparent film can be applied over embossed face designs and logos without loss of fine detail.

The manner of making and using the instant invention will now be generally described so as to enable a person skilled in the art of pharmaceutical development to make and use the same, as follows.

Special coating conditions are required to carry out the method aspect of the invention. Very large volumes of warm or heated air are required for the rapid evaporation of moisture to prevent the chemical decomposition of the aspirin as a result of being exposed to aqueous solutions during the coating operation. Rapid moisture evaporation is also essential to prevent the physical disintegration and destruction of the tablet during the coating procedure. Since aspirin tablets are relatively soft, fragile, and their surfaces and edges are easily damaged by the attrition encountered in conventional coating pans, specially designed pans capable of an efficient but gentle mixing action are required.

This complex action may be obtained by using large (<120 cm) diameter coating pans operating at unusually slow speeds of about 2.5 to 8.0 rpm, equipped with smooth baffles only slightly inclined to the direction of rotation. The tablets are thoroughly mixed with new surfaces being constantly exposed to the spray guns, but the tablets are never lifted and dropped. Efficient mixing action is necessary to obtain a uniformly coated product when operating at such slow speeds of rotation.

The preferred hydroxypropyl methylcellulose used in the method aspect of the invention is known as hydroxypropyl methylcellulose 2910, a propylene glycol ether of methylcellulose containing not less than 28.0% and not more than 30.0% of methoxy (—$OCH_3$), and not less than 7.0% and not more than 12.0% of hydroxypropoxy (—$OCH_2CHOHCH_3$), calculated on a dry basis. The preferred hydroxypropyl methylcellulose produces a viscosity between 12.0 cps and 18.0 cps when measured as a 2% by weight aqueous solution. Other viscosities down to 3 cps are satisfactory. Acceptable coating solution compositions range from 2% to 15% by weight of hydroxypropyl methylcellulose, preferred concentrations being between 4% and 8% by weight.

A variety of plasticizers may be advantageously employed in the coating solution, preferably at a concentration of about 15% to 25% w/w based on the weight of hydroxypropyl methylcellulose. Glyceryl triacetate is the preferred plasticizer; other suitable plasticizers are glycerin, propylene glycol, dibutyl sebacate, polyethylene glycol 4,000 or 6,000, and the like.

Optionally, additional ingredients can be added to the coating solution, e.g., colorants, flavors, sweetening agents, deodorants, defoaming agents, stabilizing agents, antioxidants, preservatives, surfactants and opacifying agents.

The aqueous film coating solutions are prepared by adding the plasticizer to approximately one-third the volume of purified water with rapid agitation; heat the mixture and add the hydroxypropyl methylcellulose with rapid agitation to disperse the ingredients; add the remaining two thirds volume of purified water cold with agitation to dissolve. Allow the solution to stand to deaerate. If dyes, pigments, flavorants, deodorants, surfactants, sweetening agents, antioxidants, preservatives or defoaming agents are desired, they may be added at this point. The aqueous coating solutions are then ready for application to the aspirin tablets.

In practicing the method aspect of the invention, the following tablet-coating equipment was preferably used.

Coating Pan—ACCELA-COTA ® Model 48 or 60 (Thomas Engineering, Inc., Hoffman Estates, Illinois) equipped with a 48-inch (122 cm) or 60-inch (152 cm) coating pan operating at a rotational speed of about 2.5 to 8.0 rpm and providing 1500 to 4000, cu ft/min (cfm) of inlet air at a temperature ranging from about 35° C. to 90° C., preferably 60° C. to 80° C., with exhaust air measured at about 2000 to 5000 cfm, the temperature ranging from about 35° C. to 80° C., preferably about 50° C. to 70° C.

Spraying Unit—Airless Nordson Versa-Spray Circulating Hydraulic Pump, Model 100060, manufactured by Nordson Corporation of Amherst, Ohio, operating at 650 lbs. hydraulic pressure. Two or three automatic spray guns each fitted with nozzles having an orifice diameter of 0.011" and a 0.009" turbulence plate are used to deliver a uniform spray pattern across the tablet bed. The nozzle has an orifice of 0.011" and produces a fanned spray pattern approximately 14" wide at a distance of 12" when operating under a pressure of 500 psi.

Control Unit (For the Nordson Airless Spray Unit)—Spray cycles are controlled through an automated timing panel, components of which are manufactured by Eagle Signal Manufacturing Division, Gulf & Western Industries, Inc., Davenport, IA 52803.

Spraying Unit-Air—Graco Model 953-887 Portable Tablet Coater Volumetric/Timed Spray Air/Airless, manufactured by Graco Inc. of Franklin Park, Illinois. Two or three automatic air spray guns Model 210744 each fitted with a 1.40 mm diameter nozzle and 1.17 mm needle to produce a fanned spray pattern of 15" wide at a distance of 8".

Control Unit (For the Graco Unit)—The air guns are controlled (continuous spray mode) via an automated air powered timing panel manufactured by Graco, Inc.

The following examples will further illustrate the invention without, however, limiting it thereto.

EXAMPLE 1

1.25 kg. of hydroxypropyl methylcellulose 15 cps and 0.25 kg. of triacetin are rapidly agitated in 8 kg. of hot purified water. 15.5 kg. of cold purified water is added with agitation to dissolve. Allow solution to deaerate before using. The solution is prepared in excess to allow for losses to the pan, exhaust and spray equipment.

The resulting coating solution has the following composition:

|  | w/w% |
|---|---|
| Hydroxypropyl methylcellulose 15 cps | 5.0 |
| Triacetin (glyceryl triacetate) | 1.0 |
| Purifed Water | 94.0 |
|  | 100.0 |

Prepare uncoated aspirin tablets, each containing 325 mg. aspirin, having the appropriate logo and having the following composition.

|  | w/w% |
|---|---|
| Aspirin | 80 |
| Starch | 20 |
|  | 100 |

125 kg. of uncoated tablets, each weighing 405 mg., are placed in a 48″ ACCELA COTA, and are dedusted and preheated.

The film coating solution is applied via a Nordson Airless Spray System utilizing two automatic spray guns and an intermittant spray process.

Total application time is slightly over one hour.

A total of 4 mg. of film is applied per tablet.

EXAMPLE 2

The aqueous coating solution and preparation are the same as in Example 1.

|  | w/w% |
|---|---|
| Hydroxypropyl methylcellulose 15 cps | 5.0 |
| Triacetin | 1.0 |
| Purified Water | 94.0 |
|  | 100.0 |

Prepare 125 kg. of uncoated aspirin tablets, each containing 325 mg. aspirin, having the appropriate logo and having the following composition:

|  | w/w% |
|---|---|
| Aspirin | 80 |
| Starch | 20 |
|  | 100 |

Individual uncoated tablet weight is 405 mg.

Place uncoated tablets in a 48″ ACCELA COTA, dedust and preheat.

The aqueous film coating solution is applied via a Graco Air System utilizing two automatic air spray guns and a continuous spray process.

Total application time is slightly less than one hour (50 minutes).

A total of 4 mg. of film is applied per tablet.

EXAMPLE 3

1.2 kg. of hydroxypropyl methylcellulose 15 cps and 0.24 kg. of triacetin are rapidly agitated in 9.56 kg. of hot purified water. 19.0 kg. of cold purified water is added with agitation to dissolution. Allow solution to deaerate before using. The solution is prepared in excess to allow for losses to the pan, exhaust, and spray equipment.

The resulting aqueous coating solution has the following composition:

|  | w/w% |
|---|---|
| Hydroxypropyl methylcellulose 15 cps | 4.0 |
| Triacetin | 0.8 |
| Purified Water | 95.2 |
|  | 100.0 |

Prepare aspirin tablets (325 mg. aspirin each) having the appropriate logo and the following composition:

|  | w/w% |
|---|---|
| Aspirin | 80 |
| Starch | 20 |
|  | 100 |

Individual uncoated tablet weight is 405 mg. 125 kg. of tablets are placed in a 48″ ACCELA COTA, and are dedusted and preheated.

The aqueous film coating solution is applied via a Nordson Airless Spray System utilizing two automatic spray guns and an intermittent spray process.

Total application time is slightly over one hour.

A total of 4 mg. of film is applied per tablet.

EXAMPLE 4

The aqueous coating solution and preparation are the same as in Example 3.

|  | w/w% |
|---|---|
| Hydroxypropyl methylcellulose 15 cps | 4.0 |
| Triacetin | 0.8 |
| Purified Water | 95.2 |
|  | 100.0 |

Prepare aspirin tablets (325 mg. aspirin each) having the appropriate logo and the following composition:

|  | w/w% |
|---|---|
| Aspirin | 80 |
| Starch | 20 |
|  | 100 |

Individual tablet weight uncoated is 405 mg. 125 kg. of tablets are placed in a 48″ ACCELA COTA, and are dedusted and preheated.

The aqueous film coating solution is applied via a Graco Air System utilizing two automatic air spray guns and a continuous spray process.

Total application time is about one hour.

A total of 4 mg. of film is applied per tablet.

EXAMPLE 5

1.2 kg. of hydroxypropyl methylcellulose 15 cps and 0.24 kg. of triacetin are rapidly agitated in 6.56 kg. of hot purified water. 12.0 kg. of cold purified water is added with agitation to dissolve. Allow solution to deaerate before using. The solution is prepared in excess to allow for losses to the pan, exhaust, and spray equipment.

The resulting solution has the following composition:

| | w/w% |
|---|---|
| Hydroxypropyl methylcellulose 15 cps | 6.0 |
| Triacetin | 1.2 |
| Purified Water | 92.8 |
| | 100.0 |

Prepare uncoated aspirin tablets (500 mg. aspirin each) with the following composition:

| | w/w% |
|---|---|
| Aspirin | 80 |
| Starch | 20 |
| | 100 |

Individual uncoated tablet weight is 623 mg.

125 kg. of tablets are placed in a 48" ACCELA COTA, and are dedusted and preheated.

The aqueous film coating solution is applied via a Nordson Airless Spray System utilizing two automatic spray guns and an intermittant spray process.

Total application time is slightly over one hour.

A total of 6 mg. of film is applied per tablet.

EXAMPLE 6

The aqueous coating solution and preparation are the same as in Example 5.

| | w/w% |
|---|---|
| Hydroxypropyl methylcellulose 15 cps | 6.0 |
| Triacetin | 1.2 |
| Purified Water | 92.8 |
| | 100.0 |

Prepare uncoated aspirin tablets (500 mg. aspirin each) with the following composition:

| | w/w% |
|---|---|
| Aspirin | 80 |
| Starch | 20 |
| | 100 |

Individual uncoated tablet weight uncoated is 623 mg.

125 kg. of tablets are placed in a 48" ACCELA COTA, and are dedusted and preheated.

The aqueous film coating solution is applied via a Graco Air System utilizing two automatic air spray guns and a continuous spray process.

Total application time is less than one hour.

A total of 6 mg. of film is applied per tablet.

EXAMPLE 7

2.5 kg. of hydroxypropyl methylcellulose 15 cps and 0.5 kg. triacetin are rapidly agitated in 16 kg. of hot purified water. 31 kg. of cold purified water is added with agitation to dissolve. Allow solution to deaerate before using. The solution is prepared in excess to allow for losses to the pan exhaust, and spray equipment.

The resulting aqueous coating solution has the following composition:

| | w/w% |
|---|---|
| Hydroxypropyl methylcellulose 15 cps | 5.0 |
| Triacetin | 1.0 |
| Purified Water | 94.0 |
| | 100.0 |

Prepare 280 kg. of uncoated aspirin tablets (325 mg. aspirin each) with the following composition:

| | w/w% |
|---|---|
| Aspirin | 80 |
| Starch | 20 |
| | 100 |

Individual uncoated tablet weight is 405 mg.

280 kg. of uncoated tablets are placed in a 60" ACCELA COTA, and are dedusted and preheated.

The aqueous film coating solution is applied via a Graco Air System utilizing three automatic air spray guns and a continuous spray process.

Total application time is about one and one half hours.

A total of 4 mg. of film is applied per tablet.

EXAMPLE 8

1.2 kg. of hydroxypropyl methylcellulose 6 cps and 0.24 kg. of triacetin are rapidly agitated in 4.56 kg. of hot purified water. 9 kg. of cold purified water is added with agitation to dissolve. Allow solution to deaerate before using. The solution is prepared in excess to allow for losses to the pan, exhaust, and spray equipment.

The resulting aqueous coating solution has the following composition:

| | w/w% |
|---|---|
| Hydroxypropyl methylcellulose 6 cps | 8.0 |
| Triacetin | 1.6 |
| Purified Water | 90.4 |
| | 100.0 |

Prepare uncoated aspirin tablets (325 mg. aspirin each) with the following composition:

| | w/w% |
|---|---|
| Aspirin | 80 |
| Starch | 20 |
| | 100 |

Individual tablet weight uncoated is 405 mg.

125 kg. of uncoated tablets are placed in a 48" ACCELA COTA, and are dedusted and preheated.

The aqueous film coating solution is applied via a Graco Air System utilizing two automatic air spray guns and a continuous spray process.

Total application time is less than forty five minutes.

A total of 4 mg. of film is applied per tablet.

The coated tablets of Examples 1–8 disintegrate (USP method) in less than one minute; their moisture levels range from 1–2%; and their NAS (non-aspirin salicylate) content meets USP specifications. Surprisingly, it was found that the moisture content of the coated tablets in some instances actually was less than moisture content of the uncoated tablets.

We claim:

1. The method for preparing an easily-swallowed, powder-free, gastric-disintegrable and thinly-coated aspirin tablet which does not have the characteristic aspirin taste and does not produce the esophageal discomfort of an uncoated aspirin tablet and which does not disintegrate in the stomach materially slower than the uncoated aspirin tablet, which comprises aqueous spray-coating hydroxypropyl methylcellulose onto all exterior surfaces of an aspirin tablet, the amount of hydroxypropyl methylcellulose being between 0.5 and 2.0 parts by weight per 100 parts by weight of the aspirin tablet.

2. The method for preparing an easily-swallowed, powder-free, gastric-disintegrable and thinly-coated aspirin tablet which comprises spraying an aqueous solution of hydroxypropyl methylcellulose onto uncoated aspirin tablets in a slowly rotating baffled pan in a chamber equipped to measure and control both inlet and outlet air flow rates and temperatures, the inlet and outlet air rates and temperatures being sufficient to insure rapid evaporation of the water and to provide an evenly-applied thin coating of hydroxypropyl methylcellulose onto the uncoated tablets without causing their decomposition and/or physical disintegration.

3. The method according to claim 2 where the pan is rotated at about 2.5 to 8.0 rpm, the inlet air flow rate is maintained at about 1500 to 4000 cubic feet per minute at a temperature ranging from about 35° C. to 90° C. and the outlet air flow rate is maintained at about 2000 to 5000 cubic feet per minute at a temperature ranging from about 35° C. to 80° C.

4. The method according to claim 2 where the dew point of the inlet air is monitored and regulated at about 2° C. to 15° C. and the air is filtered to remove dust and any other contaminants.

5. The method according to claim 2 where a 48" perforated coating pan is used, the inlet air flow rate is maintained within the range of about 1700 to 2500 cubic feet per minute at a temperature range of about 60° C. to 80° C. and the outlet air flow rate is maintained within the range of about 2100 to 2700 cubic feet per minute at a temperature range of about 50° C. to 70° C.

6. The method according to claim 2 using a 2% to 15% by weight solution of hydroxypropyl methylcellulose in water.

7. The method according to claim 2 using a 4% to 8% by weight solution of hydroxypropyl methylcellulose in water.

8. The method according to claim 2 using a 2% to 15% by weight solution of hydroxypropyl methylcellulose in water containing about 15% to 25% w/w of a plasticizer based on the weight of hydroxypropyl methylcellulose.

9. The method according to claim 2 using a 4% to 8% by weight solution of hydroxypropyl methylcellulose in water containing about 15% to 25% w/w of glyceryl triacetate as plasticizer based on the weight of hydroxypropyl methylcellulose.

10. An easily-swallowed, powder-free and gastric-disintegrable aspirin tablet thinly-coated on all of its exterior surfaces with hydroxypropyl methylcellulose, said coating being sufficiently thin as to not materially alter the gastric rate of disintegration as compared with the uncoated aspirin tablet, and which coated tablet does not have the characteristic aspirin taste and does not produce the esophageal discomfort of the uncoated aspirin tablet.

11. The aspirin tablet according to claim 10 which is uniformly coated with about 0.5 to 2 parts by weight of hydroxypropyl methylcellulose per 100 parts by weight of the aspirin tablet.

12. The aspirin tablet according to claim 10 or 11 where the hydroxypropyl methylcellulose contains not less than 28.0% and not more than 30.0% of methoxy and not less than 7.0% nor more than 12.0% of hydroxypropoxy.

13. The aspirin tablet according to claim 10 or 11 where hydroxypropyl methylcellulose produces a viscosity between 13.0 and 18.0 centipoises when measured as a 2% by weight aqueous solution.

14. The aspirin tablet according to claim 10 or 11 where the hydroxypropyl methylcellulose contains about 15 to 25% w/w of a plasticizer based on the weight of hydroxypropyl methylcellulose.

15. The aspirin tablet according to claim 10 or 11 where hydroxypropyl methylcellulose contains about 15 to 25% w/w of glyceryl triacetate as plasticizer based on the weight of hydroxypropyl methylcellulose.

16. The thinly-coated aspirin tablet when produced by the method of claim 1.

17. The thinly-coated aspirin tablet when produced by the method of claim 2.

18. The thinly-coated aspirin tablet when produced by the method of claim 3.

19. The thinly-coated aspirin tablet when produced by the method of claim 4.

20. The thinly-coated aspirin tablet when produced by the method of claim 5.

21. The thinly-coated aspirin tablet when produced by the method of claim 6.

22. The thinly-coated aspirin tablet when produced by the method of claim 7.

23. The thinly-coated aspirin tablet when produced by the method of claim 8.

24. The thinly-coated aspirin tablet when produced by the method of claim 9.

* * * * *

UNITED STATES PATENT AND TRADEMARK OFFICE
CERTIFICATE OF CORRECTION

PATENT NO. : 4,302,440

DATED : November 24, 1981

INVENTOR(S) : Phillip M. John, Raymond J. Belanger and Myron Paikoff

It is certified that error appears in the above-identified patent and that said Letters Patent are hereby corrected as shown below:

Column 4, line 47, "is" should read -- if --.

Column 5, line 42, "<120" should read -- >120 --.

Signed and Sealed this

Twenty-third Day of November 1982

[SEAL]

Attest:

GERALD J. MOSSINGHOFF

Attesting Officer    Commissioner of Patents and Trademarks

UNITED STATES PATENT AND TRADEMARK OFFICE
CERTIFICATE OF CORRECTION

PATENT NO. : B1 4,302,440
DATED : August 5, 1986
INVENTOR(S) : Phillip M. John, Raymond Belanger & Myron Paikoff It is certified that error appears in the above-identified patent and that said Letters Patent is hereby corrected as shown below:

On the face page in the title after "TABLET" insert -- HAVING FINE DETAIL IN EMBOSSED FACE DESIGNS AND LOGOS --.

On the face page immediately after the title amend "Phillip M., John" to read -- Phillip M. John --.

Column 1, line 30 insert -- The patentability of claims 3-5, 7 and 9 is confirmed. --.

Column 2, lines 2-3 "aspirin tablets coated with hydroxypropyl methylcellulose," should be printed in italics.

Signed and Sealed this

Eighteenth Day of August, 1987

*Attest:*

DONALD J. QUIGG

*Attesting Officer*  *Commissioner of Patents and Trademarks*

REEXAMINATION CERTIFICATE (548th)

United States Patent [19]

John, Phillip M. et al.

[11] B1 4,302,440

[45] Certificate Issued  Aug. 5, 1986

[54] EASILY-SWALLOWED, POWDER-FREE AND GASTRIC-DISINTEGRABLE ASPIRIN TABLET THINLY-COATED WITH HYDROXYPROPYL METHYLCELLULOSE AND AQUEOUS SPRAY-COATING PREPARATION THEREOF

[75] Inventors: Phillip M., John, East Greenbush; Raymond J. Belanger, Rensselaer; Myron Paikoff, Colonie, all of N.Y.

[73] Assignee: Sterling Drug Inc., New York, N.Y.

Reexamination Request:
No. 90/000,831, Aug. 8, 1985

Reexamination Certificate for:
Patent No.: 4,302,440
Issued: Nov. 24, 1981
Appl. No.: 174,249
Filed: Jul. 31, 1980

Certificate of Correction issued Nov. 23, 1982.

[51] Int. Cl.³ .............................................. A61K 9/36
[52] U.S. Cl. .......................................... 424/35; 427/3
[58] Field of Search ............................... 424/35; 427/3

[56] References Cited

U.S. PATENT DOCUMENTS 3,371,015  2/1968  Sjogren et al. ....................... 424/35
3,383,236  5/1968  Brindamour ......................... 424/35
4,302,440  11/1981  John et al. ............................ 424/35

FOREIGN PATENT DOCUMENTS 1444890  8/1976  United Kingdom .
B1444890  9/1977  United Kingdom .
753851  6/1975  South Africa .

OTHER PUBLICATIONS

J. F. Pickard et al., J. Pharm. Pharmacol. 28 Supplement 20P (1976).
H. Zeller and Tonedachi, four-page paper entitled "Aqueous Film Coating", presented as talk given Mar. 30, 1977 at meeting in Philadelphia, Pa.
Shin-etsu/Biddle Sawyer nine-page bulletin, undated but in possession of inventors of U.S. Patent 4,302,440 prior to its filing date).
Shin-etsu four-page Technical Information bulletin dated Mar. 25, 1975.
Delporte and Jaminet, Chem. Abstrs. 90. 61138f (1979).
1979 J. F. Pickard Ph.D. Thesis, Title page, prelim. pp. I-XV, pp. 1-199 and appendix (pp. A-1 through A-3).
1977 Dow Chemical Co. bulletin (13 pages plus front and back covers).
Thomas Engineering Inc. 1976 Jun. 30 eight-page bulletin, courtesy of Manesty Machines Ltd.
R. C. Rowe, J. Pharm. Pharmac. 30, 343-346; 669-672 (1978).
R. C. Rowe, Pharm. Acta Helv. 51, 330-334 (1976).
Schwartz and Alvino, J. Pharm. Sci. 65, 572-575 (1976).

*Primary Examiner*—Shep K. Rose

[57]  ABSTRACT

A method for preparing an easily-swallowed, powder-free, gastric-disintegrable and thinly-coated aspirin tablet, which does not have the characteristic aspirin taste, does not produce the esophageal discomfort of an uncoated aspirin tablet and does not disintegrate in the stomach materially slower than the uncoated aspirin tablet, which comprises aqueous spray-coating hydroxypropyl methylcellulose onto all exterior surfaces of an aspirin tablet, the amount of hydroxypropyl methylcellulose being between 0.5 and 2.0 parts by weight per 100 parts by weight of the aspirin tablet. An aqueous solution of 2% to 15% by weight of hydroxypropyl methylcellulose and about 15% to 25% w/w of a plasticizer based on hydroxypropyl methylcellulose is sprayed onto uncoated aspirin tablets in a slowly rotating baffled pan in a chamber equipped to measure and control both inlet and outlet air flow rates and both inlet and outlet air temperatures, said air flow rates and temperatures being sufficient to insure rapid evaporation of the water and to provide an evenly-applied thin coating of hydroxypropyl methylcellulose onto the uncoated tablets without causing their decomposition and/or physical disintegration. Preferred pan-rotation speeds, inlet and outlet air flow rates and temperatures are given. Other aspects of the invention are said thinly-coated tablets and said coated tablets when produced by said aqueous spray-coating method.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 5, line 65 to column 6, line 3:
Glyceryl triacetate as plasticizer is [A variety of plasticizers may be advantageously] employed in the coating solution, preferably at a concentration of about 15% to 25% w/w based on the weight of hydroxypropyl methylcellulose. [Glyceryl triacetate is the preferred plasticizer; other suitable plasticizers are glycerin, propylene glycol, dibutyl sebacate, polyethylene glycol 4,000 or 6,000, and the like.]

AS A RESULT OF REEXAMINATION, IT HAS BEEN DETERMINED THAT:

Claims 6, 8, 11, 14, 15, 21 and 23 are cancelled.

Claims 1, 2, 10, 12, 13, 16–20, 22 and 24 are determined to be patentable as amended.

1. [The] *In a* method for preparing [an] *aspirin tablets coated with hydroxypropyl methylcellulose,* [easily-swallowed, powder-free, gastric-disintegrable and thinly-coated aspirin tablet which does not have the characteristic aspirin taste and does not produce the esophageal discomfort of an uncoated aspirin tablet and which does not disintegrate in the stomach materially slower than the uncoated aspirin tablet,] *the uncoated tablets of which are relatively soft, fragile and whose surfaces and edges are easily damaged by the attrition encountered in conventional coating pans, which have not been specially treated or reformulated to increase hardness or durability to withstand breakage during film-coating manipulations and which have fine detail in embossed face designs and logos, the improvement* which comprises [aqueous spray-coating] *a one-step method, applicable for commercial production, of spraying a 2% to 15% by weight solution of* hydroxypropyl methylcellulose *in water containing about 15% to 25% w/w of glyceryl triacetate as plasticizer based on the weight of hydroxypropyl methylcellulose* onto all exterior surfaces of [an] uncoated aspirin [tablet] *tablets, which have been dedusted and preheated, to provide a slick shiny transparent film of hydroxypropyl methylcellulose with plasticizer without loss of fine detail in embossed face designs and logos, the resulting coated tablets being easily-swallowed, powder-free, gastric-disintegrable and thinly-coated, not having the characteristic aspirin taste, not producing the esophageal discomfort of uncoated aspirin tablets and not disintegrating in the stomach materially slower than the uncoated aspirin tablets,* the amount of hydroxypropyl methylcellulose being between 0.5 and 2.0 parts by weight per 100 parts by weight of the aspirin tablet.

2. [The] *In a* method for preparing [an] aspirin tablets coated with hydroxypropyl methylcellulose, [easily-swallowed, powder-free, gastric-disintegrable and thinly-coated aspirin tablet] *the uncoated tablets of which are relatively soft, fragile and whose surfaces and edges are easily damaged by the attrition encountered in conventional coating pans, which have not been specially treated or reformulated to increase hardness or durability to withstand breakage during film-coating manipulations and which have fine detail in embossed face designs and logos, the improvement* which comprises spraying [an aqueous] *a 2% to 15% by weight* solution *in* hydroxypropyl methylcellulose *in water containing about 15% to 25% w/w of glyceryl triacetate as plasticizer based on the weight of hydroxypropyl methylcellulose* onto *said* uncoated aspirin tablets in a slowly rotating baffled pan in a chamber equipped to measure and control both inlet and outlet air flow rates and temperatures, the inlet and outlet air rates and temperatures being sufficient to insure rapid evaporation of the water and to provide an evenly-applied [thin coating] *slick shiny transparent film* of hydroxypropyl methylcellulose *with plasticizer* onto *all exterior surfaces of* the uncoated tablets *without loss of fine detail in embossed face designs and logos and* without causing their decomposition and/or physical disintegration[.]*,* *the thinly-coated aspirin tablet being easily-swallowed, powder-free and gastric-disintegrable, and the amount of hydroxypropyl methylcellulose being between 0.5 and 2.0 parts by weight per 100 parts by weight of the aspirin tablet.*

10. An easily-swallowed, powder-free and gastric-disintegrable aspirin tablet *having fine detail in embossed face designs and logos* [thinly-coated] *having a slick shiny transparent film* on all of its exterior surfaces [with] *of* hydroxypropyl methyl cellulose *and plasticizer, said tablet being uniformly coated with about 0.5 to 2 parts by weight of hydroxypropyl methylcellulose per 100 parts by weight of the aspirin tablet, where the hydroxypropyl methylcellulose contains about 15 to 25% w/w of glyceryl triazetate as plasticizer based on the weight of hydroxypropyl methylcellulose,* said coating being sufficiently thin as to not materially alter the gastric rate of disintegration *or cause loss of fine detail in embossed face designs and logos* as compared with the [uncoated aspirin] tablet *prior to coating,* and which coated tablet does not have the characteristic aspirin taste and does not produce the esophageal discomfort of the [uncoated] aspirin tablet *prior to coating.*

12. The aspirin tablet according to claim 10 [or 11] where the hydroxypropyl methylcellulose contains not less than 28.0% and not more than 30.0% of methoxy and not less than 7.0% nor more than 12.0% of hydroxypropoxy.

13. The aspirin tablet according to claim 10 [or 11] where hydroxypropyl methylcellulose produces a viscosity between 13.0 and 18.0 centipoises when measured as a 2% by weight aqueous solution.

16. The thinly-coated aspirin tablet, *having fine detail in embossed face designs and logos* when produced by the method of claim 1.

17. The thinly-coated aspirin tablet, *having fine detail in embossed face designs and logos* when produced by the method of claim 2.

18. The thinly-coated aspirin tablet, *having fine detail in embossed face designs and logos* when produced by the method of claim 3.

19. The thinly-coated aspirin tablet, *having fine detail in embossed face designs and logos* when produced by the method of claim 4.

20. The thinly-coated aspirin tablet, *having fine detail in embossed face designs and logos* when produced by the method of claim 5.

22. The thinly-coated aspirin tablet, *having fine detail in embossed face designs and logos* when produced by the method of claim 7.

24. The thinly-coated aspirin tablet, *having fine detail in embossed face designs and logos* when produced by the method of claim 9.

* * * * *